ized antihemophlic factor (AHF) concentrate. The product is prepared by use of a semi-permeable membrane apparatus that desalts the plasma to between 45 to 80% of its salt content while constantly maintaining the plasma at substantially its original starting pH level. Under these conditions the AHF portion of the plasma will precipitate.

United States Patent [19]
Pabst et al.

[11] 4,435,318
[45] Mar. 6, 1984

[54] ELECTRODIALYSIS PREPARATION OF PURIFIED AHF CONCENTRATE

[75] Inventors: Patrea L. Pabst, Jamaica Plain; David H. Bing, Brookline, both of Mass.

[73] Assignee: Ionics, Incorporated, Watertown, Mass.

[21] Appl. No.: 266,400

[22] Filed: May 22, 1981

[51] Int. Cl.³ .............................................. C07G 7/00
[52] U.S. Cl. ................................. 260/112 B; 424/101; 204/180 R
[58] Field of Search .................... 260/112 B, 112 R; 424/101; 204/180 R

[56] References Cited

U.S. PATENT DOCUMENTS

| | | | |
|---|---|---|---|
| 2,999,791 | 9/1961 | Fowell | 167/74 |
| 3,234,199 | 2/1966 | Reid | 260/112 |
| 3,943,245 | 3/1976 | Silverstein | 424/101 |
| 3,972,791 | 8/1976 | Stern | 204/180 R |
| 4,069,216 | 1/1978 | Shambrom | 260/112 B |
| 4,081,432 | 3/1978 | Delente | 260/112 B |
| 4,188,318 | 2/1980 | Shanbrom | 260/112 B |
| 4,276,140 | 6/1981 | Jain | 204/180 P |
| 4,321,192 | 3/1982 | Jain | 260/122 |
| 4,322,275 | 3/1982 | Jain | 204/180 P |
| 4,348,315 | 9/1982 | Blomback | 424/101 |

OTHER PUBLICATIONS

Morris C. J. O. R., *Separation Methods in Biochemistry* 1976, pp. 923–927.
Putnam, Frank W., "The Plasma Proteins" 2nd edition, vol. III, Academic Press New York, 1977, pp. 562–565.

*Primary Examiner*—John C. Bleutge
*Assistant Examiner*—Patricia Short
*Attorney, Agent, or Firm*—Norman E. Saliba

[57] ABSTRACT

A process is described for the preparation of a novel protein product of a highly purified antihemophlic factor (AHF) concentrate. The product is prepared by use of a semi-permeable membrane apparatus that desalts the plasma to between 45 to 80% of its salt content while constantly maintaining the plasma at substantially its original starting pH level. Under these conditions the AHF portion of the plasma will precipitate.

10 Claims, No Drawings

ELECTRODIALYSIS PREPARATION OF PURIFIED AHF CONCENTRATE

FIELD OF INVENTION

This invention relates to the separation, recovery and concentration of antihemophiliac factors from blood plasma derivatives and the novel product obtained thereby.

BACKGROUND AND PRIOR ART

Factor VIII and von Willebrand's factor are associated plasma proteins that together are called Antihemophlic Factor (AHF). Both are important in the blood clotting mechanism. Factor VIII serves as a co-factor along with calcium and phospholipid to enable Factor $IX_a$ to cleave zymogen Factor X to thus activate Factor X, all being a part of the complex coagulation cascade system. Von Willebrand's factor (vWF) apparently acts in the aggregation of platelets which provide the necessary phospholipid. The absence of either of these factors may result in prolonged bleeding times. Factor V also serves an important role in the coagulation system by aiding activated Factor X in the cleavage of prothrombin to thrombin. (*The Plasma Proteins, Vol. III, 2nd Ed., Structure, Function, Genetic Control* (1977) (*Academic Press, Inc., N.Y.*) p. 422–544.)

Several methods of making concentrates of AHF are in current use. These range from simply freezing and then thawing plasma (cryoprecipitation) to yield a more concentrated insoluble mixture of Factor VIII, fibrinogen, cold-insoluble globulin to more involved procedures, etc. These concentrates may be made more highly purified by further treatment employing techniques such as aluminum hydroxide absorbtion, glycine extraction, polyethylene glycol concentration, filtration, etc. Difficulties associated with these highly purified concentrates may for example include a loss of the Factor VIII clotting activity and/or an increase in the percentage of unwanted alloagglutinins. (I. M. Nilsson; L. Holmberg; P. Seenberg; P. Menrichson, Scand. J. Haematology 24: 340–349 (1980), Allain, J. P.; F. Vervoust; J. P. Soulier, Vox Sang. 38: 68–80 (1980).

THE INVENTION

The present invention is directed to methods of preparing novel antihemophlic concentrate products from either fresh or thawed frozen citrated plasma (having a pH normally between 6.0–8.5) that is substantially free of contaminants found in presently available antihemophlic concentrates. Sodium citrate is the preferred anticoagulant for the plasma since this was found to yield a product having the least amount of contaminants.

This application discloses an invention which is in improvement over that disclosed in co-pending Application No. 256,264 filed Apr. 21, 1981 in the name of S. Jain; both applications being assigned to a common assignee. This co-pending application discloses a process for desalting a plasma protein solution by dialysis for the purpose of separating and recovering the antihemophiliac factor (AHF). In the present invention, however, the pH of the plasma and the degree of salt removal is carefully controlled so as to produce an AHF product or concentrate having varied protein components in a most desired concentration and/or proportion along with improved product purity.

The following describes the various plasma specific proteins other than AHF which is found in precipitates that result from the removal of salts from plasma in accordance with the process of the present invention.

Factor V is a very large molecular weight glycoprotein. It behaves similar to Factor VIII by acting as a co-factor to Factor $X_a$ along with calcium and phospholipid to activate prothrombin to thrombin. Deficiencies in Factor V are rare but do exist. Treatment is with fresh plasma since Factor V activity is lost by freezing. Factor V is extremely unstable and its molecular nature is a matter of controversy.

Factor IX is a vitamin K dependent protein that is important in coagulation. Its activated form serves in the intrinsic pathway to activate Factor X to Factor $X_a$ with the aid of Factor VIII, calcium, and phospholipid. It may be able to act without Factor VIII to initiate coagulation but this activity is not well understood. Deficiency of this factor results in a disease called Hemophilia B or "Christmas disease". Factor IX is frequently found associated with Factor VIII concentrates and may be specifically removed by adsorbtion onto barium citrate.

Factor X is another vitamin K dependent glycoprotein synthesized by the liver. It plays a critical role in blood coagulation by linking the intrinsic (Factor XII initiated coagulation) and the extrinsic (Factor VII and tissue factor) coagulation pathways. It circulates in a zymogen form that is activated by thrombin, Factor $IX_a$, or Factor VII (the extrinsic pathway). Vitamin K dependent proteins may be specifically removed by adsorbtion onto barium citrate.

Plasmin is a proteolytic enzyme generated from plasminogen by specific activators, in particular by urokinase found in plasma. Plasmin is inhibited by Antithrombin III, $\alpha$2-macroglobulin, $\alpha$1-antitrypsin, $\alpha$2 plasmin inhibitor and $Cl^{31}$ inactivator. Since plasmin can act as an activator of Factor XII (Hageman factor) which initiates the entire clotting system, it is imperative the plasmin not be a contaminate of antihemophiliac concentrates. Plasmin is also used as a physiological agent to dissolve fibrin clots resulting from the normal coagulation process. Plasminogen removal may be accomplished by use of an affinity column of lysine sepharose.

Fibrinogen is a large (340,000 molecular weight) globulin-like molecule found in normal human plasma at levels of 2 to 4 mg/ml. It is the protein that is least soluble after freezing, after ethanol extraction, or after aluminum hydroxide adsorbtion. The usual Factor VIII precipitates are normally contaminated with fibrinogen along with plasminogen, and Factor XIII (fibrin stabilizing factor). Fibrinogen precipitates formed by freezing are highly insoluble and require strong salt solutions (typically 3 M NaCl) to dissolve them. The most common method for removal of insoluble fibrinogen is through the use of a filter.

Commercially available, Factor VIII preparations contain antibodies to red cell antigens A and B. These antibodies (alloagglutinins) have been implicated in cases where hemolysis had developed in patients receiving these Factor VIII preparations. These antibodies are directed against red cell antigens A and B, and cause red cells to clump and become subject to lysis when the immunoglobulins attach to the cells' surface. These antibodies are of both Immunoglobulin G and Immunoglobulin M classes, although there is no direct correlation between the concentration of immunoglobulin and that of alloaglutinins.

This invention involves the use of a continuous flow system whereby the salt concentration of the plasma protein solution is decreased by the removal of salts (ions) through semi-permeable membrane systems such as by electrodialysis, dialysis, and/or ultrafiltration systems. Electrodialysis (ED) equipment and methods of operation are more fully described in U.S. Pat. Nos. 2,848,403; 2,863,813; 3,003,940; 3,341,441; 4,115,225 and others. An electrodialysis stack normally comprises one or more pairs of a salt concentrating and salt diluting chamber separated by alternating anion and cation selective membranes. One or more selective membranes may at times be replaced by neutral or non-selective membranes. The chambers are located between an anode and a cathode electrode. An electrolyte solution is preferably passed through the cathode and anode chambers to conduct current across the concentrating and the diluting chambers. Usually a concentrating chamber is located so as to isolate the electrode solutions from the product or diluting chamber. The ion selective membranes are selected depending on the solution under treatment and the liquid flow rates through the stack. The applied current is carefully regulated to obtain the desired results. The plasma is passed into and through the diluting chambers and on impressing a direct current across the electrodes, the salt or ionic content of the plasma is reduced due to the passage of salt through the membranes into the adjacent concentrating chambers. The concentrating chambers may be primed initially with a small amount of NaCl electrolyte solution. The resulting desalted plasma is collected from the diluting chambers and treated to separate and remove one or more of the desired proteins.

Dialysis is another membrane separation process useable in the present invention where the driving force is a gradient in chemical potential, e.g. a gradient in concentration or activity of the solutes across the membrane separating the two solutions. The membrane employed is permeable to water and low molecular weight solutes. The solute diffuses through the membrane until the concentration gradient is negligible on both sides of the membrane. Thus dialysis can be quite an efficient process in situations where high concentration gradients are involved. The main application of the prior art dialysis is in the kidney dialysis field where low molecular weight solutes, like urea and some salts, are removed from blood. Such hemodialysis systems are fully described in U.S. Pat. Nos. 4,192,748; 4,191,646; 4,213,859; 3,960,730, and others. These patents, however, are concerned merely with reducing the salt content and low molecular weight proteins like urea, creatinine, B-12, etc. rather than using the dialysis process in a complex scheme of plasma protein fractionation for the recovery of a specific plasma component like AHF.

It has been determined that the AHF precipitate will form following removal of at least about forty-five (45) percent of the salt in the plasma (preferably as measured by conductivity). Optimum specific activity (i.e., the ratio of Factor VIII clotting activity to total protein) and increased purity and yield is obtained when about seventy (70) percent of the salt is removed from the plasma. At greater than about an eighty (80) percent removal there is found a significant level of contaminants in the resulting concentrate. It is most important that the pH of the plasma during the separation and recovery of AHF be maintained at substantially the original pH value of the starting plasma, preferably within ±0.2 pH units. This pH control is critical and in electrodialysis may be accomplished for example by the use of sodium citrate as the electrode stream solution. The temperature must remain above 0° C. to prevent cryoprecipitation and below 40° C. to avoid degradation of the AHF. Temperatures below 25° C. are preferred for situations not involving on-line separations since Factor VIII has been demonstrated to have a shorter half life at the higher temperatures.

As was previously stated, the removal of at least about 45 percent of the plasma's original salt content while maintaining the plasma at a substantially constant pH level, will result in the formation of an AHF precipitate. When this suspended precipitate is removed, it is resuspended in a volume of deionized water which volume is preferably about 10 percent of the starting volume of the plasma protein solution from which the initial precipitate was removed. The then washed precipitate is dissolved in a volume of 0.15 M sodium chloride solution (preferred volume is about 1 percent of the starting plasma volume) for use in short-term storage at 4° C. or long term storage at −70° C. or as a lyophilized product.

Factor IX, a vitamin K dependent protein which is normally found as a contaminant of the AHF concentrate, can be removed from the concentrate and purified by adsorption onto barium citrate or barium sulfate followed by elution with sodium citrate. This allows the production of a Factor IX product in a form suitable for the treatment of Christmas disease.

The following non-limiting examples illustrate the present invention.

EXAMPLE 1

Fresh acid citrate dextrose (ACD) plasma was desalted by the use of an electrodialysis apparatus to remove about 70 percent of its original salt concentration, as measured by conductivity. The original pH (6.95) of the plasma was substantially unaltered by the process, remaining substantially constant during the course of the run.

The electrodialysis apparatus employed was manufactured by Ionics, Incorporated, Watertown, Mass. It combined a 9"×10" stack of alternating anion and cation selective membranes separated by channeled fluid flow spacers with the membranes and spacers all placed between a cathode and anode electrode. A power supply capable of generating a direct current of 5 amps was used along with monitors for pH, conductivity, and temperature. Pumps served to circulate the electrode streams (initially a 2.5 percent sodium citrate solution of a pH 8 to 8.05), the salt concentrating stream (initially 0.15 percent sodium chloride solution), and the diluting or plasma stream to be desalted. The electrode solution was circulated at the rate of about 180 ml/min. and the salt concentrating and diluting steams at about 90 ml/min. per cell pair. For desalting a volume of 500 ml. of plasma (free from all cell components) two cell pairs located between the terminal electrodes were utilized, each cell pair consisting of a concentrating and diluting stream cell spacer separated by an anion or cation membrane. The liquid hold-up volume in each cell was about 22.5 mls.

After allowing all solutions to circulate and come to equilibrium, direct power was applied and maintained at a constant current of about 5 amps. The plasma conductivity was monitored until its conductivity decreased to about 30 percent of its initial conductivity value. The temperature changed only slightly over the course of the run, operating between about 16°–20° C. The run was terminated and the desalted plasma in the stack and pumps was recovered and stored at 4° C.

After 12 hours of storage, the plasma was centrifuged at approximately 5000 g for 15 minutes. The supernatant was decanted (either to be used in further preparations or for reuse as plasma after first rebalancing its lost salt content) and the recovered precipitate washed by resuspension in 50 ml of deionized water. The washed precipitate was again recovered by centrifugation and then easily dissolved in only approximately 1 percent of the original starting plasma volume by using 5 ml of 0.15 M sodium chloride. The resulting liquid contained 40 percent of the plasma's original content of Factor VIII and von Willebrand's factor. Small amounts of Factor IX, $Cl_q$ and fibrinectin were also found in the precipitate. If the starting plasma had contained normal, intact Factor V, then about the same amount (40 percent) of this material would also be present in the precipitate.

The recovered product containing the antihemophlic factor was measured for its ability to correct the clotting time of congenitally deficient Factor VIII and von Willebrand's factor plasma. The vWF antigen was measured by the Laurell immunassay technique. The presence of other proteins were determined by radialimmuno diffusion assay, immunoelectrophoresis and clotting assays using congenitally deficient plasma. It was determined that Factor VIII functional activity correlated to vWF antigenic activity in substantially a one to one ratio. The specific activity was about 0.6 of Factor VIII activity per mg. of recovered protein and there was less than 1% by weight of fibrinogen. This material was found to remain stable several days at 4° C.

EXAMPLE 2

In this Example, rapidly thawed fresh frozen citrated plasma was used as the source of antihemophlic factor. The plasma was thawed at 37° C. over a short period of time and centrifuged at 5000 g for 15 minutes. The supernatent was then desalted as described in Example 1 to again remove about 70% of the original salt content as measured by conductivity. The precipitate formed consisted of a product having substantially the same characteristics as in the previous run.

EXAMPLE 3

This Example involved the precipitation of AHF from a plasma solution followed by the immediate removal of the precipitate. The yield of recovered antihemophlic factor was approximately one-third of that described in Example 1 where the solution has been allowed to equilibrate at 4° C. for 12 hours following desalting. The concentrate obtained, however, was still essentially of the same composition as that product described in Example 1.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies and methods.

The embodiments of this invention in which an exclusive property or privilege is claimed are defined as follows:

1. A process for the separation and recovery of Factor VIII, von Willebrand's factor, and Factor V from plasma and plasma derivative streams having a pH normally between about 6 to 8.5 comprising removing from said blood stream when present substantially all initial turbidity therein, subsequently passing said blood plasma into and out of an apparatus containing one or more semi-permeable membranes which separate said plasma stream from a salt receiving stream thereby decreasing the salt content of said plasma stream between about 45 to 80% to cause the formation of a protein turbidity enriched in Factor VIII, von Willebrand's factor and Factor V, subsequently removing substantially all of said turbidity and maintaining the temperature of said plasma stream during said separation and recovery process in the range of between about 4°–40° C., and at substantially its original starting pH level.

2. A process according to claim 1 wherein the said plasma stream is anticoagulated using sodium citrate.

3. A process according to claim 1 wherein the said plasma stream is thawed fresh frozen citrated plasma.

4. A process according to claim 1 wherein said semi-permeable membrane process for decreasing said salt content comprises electrodialysis.

5. A process according to claim 1 wherein said semi-permeable membrane process for decreasing said salt content comprises dialysis.

6. A process according to claim 1 wherein said semi-permeable membrane process for decreasing said salt content comprises ultra filtration.

7. A process according to claim 1 wherein the original pH of the plasma is maintained substantially constant within ±0.2 pH units.

8. A process according to claim 1 wherein a vitamin K dependent protein when present in said protein turbidity is selectively removed therefrom by adsorbtion onto a salt selected from the group consisting of barium citrate, barium sulfate and mixtures of the same.

9. A process according to claim 8 wherein said vitamin K dependent protein is Factor IX.

10. A process according to claim 1 wherein the recovered protein turbidity comprises between about 0.5 to 2 units of Factor VIII clotting activity per mg of recovered protein, which is equivalent to between about 30 to 50 units per milliliter of protein, vWF antigenic activity in an amount whereby there is a ratio of substantially 1 to 1 vWF antigen activity to units of Factor VIII clotting activity and up to about 2 units of Factor V clotting activity per mg of recovered protein.

* * * * *